US010138171B2

(12) United States Patent
Berg et al.

(10) Patent No.: US 10,138,171 B2
(45) Date of Patent: Nov. 27, 2018

(54) METHOD FOR ALTERING PHOTOSYNTHETIC GROWTH

(71) Applicants: Stacie Z. Berg, Canandaigua, NY (US); Jonathan Rydell, Canandaigua, NY (US)

(72) Inventors: Stacie Z. Berg, Canandaigua, NY (US); Jonathan Rydell, Canandaigua, NY (US)

( * ) Notice: Subject to any disclaimer, the term of this patent is extended or adjusted under 35 U.S.C. 154(b) by 0 days.

(21) Appl. No.: 14/993,095

(22) Filed: Jan. 12, 2016

(65) Prior Publication Data

US 2017/0208816 A1  Jul. 27, 2017

Related U.S. Application Data

(60) Provisional application No. 62/104,797, filed on Jan. 18, 2015.

(51) Int. Cl.

| | | |
|---|---|---|
| *A01N 41/04* | (2006.01) | |
| *A01N 43/16* | (2006.01) | |
| *A01N 43/56* | (2006.01) | |
| *C05F 11/10* | (2006.01) | |
| *C05G 3/00* | (2006.01) | |
| *C05G 3/02* | (2006.01) | |

(52) U.S. Cl.
CPC .............. *C05F 11/10* (2013.01); *A01N 41/04* (2013.01); *A01N 43/16* (2013.01); *A01N 43/56* (2013.01); *C05G 3/00* (2013.01); *C05G 3/02* (2013.01)

(58) Field of Classification Search
None
See application file for complete search history.

(56) References Cited

U.S. PATENT DOCUMENTS

| | | |
|---|---|---|
| 2,761,868 A | 9/1956 | Lacey |
| 2,786,821 A | 3/1957 | Gardner |
| 2,870,037 A | 1/1959 | Converse |
| 2,911,157 A | 11/1959 | Converse |
| 3,352,058 A | 11/1967 | Brant |
| 4,042,367 A | 8/1977 | Wilson |
| 4,047,921 A | 9/1977 | Mues et al. |
| 4,634,555 A | 1/1987 | Baxter et al. |
| 4,698,334 A | 10/1987 | Horriere et al. |
| 4,737,515 A | 4/1988 | Hallenbach et al. |
| 5,310,725 A | 5/1994 | Putsche |
| 5,336,661 A | 8/1994 | Lucas |
| 5,352,729 A | 10/1994 | Birkhofer et al. |
| 5,599,804 A | 2/1997 | Mudge |
| 5,643,852 A | 7/1997 | Lucas et al. |
| 5,977,029 A | 11/1999 | Fischer et al. |
| 6,329,321 B2 | 12/2001 | Okura et al. |
| 6,432,877 B2 | 8/2002 | Okura et al. |
| 6,506,707 B1 | 1/2003 | Bessette |
| 6,607,589 B2 | 8/2003 | Adamic et al. |
| 7,431,743 B2 | 10/2008 | Hughes |
| 8,426,343 B2 | 4/2013 | Norton et al. |
| 8,440,230 B2 * | 5/2013 | Lelas ................... C01F 11/185 424/489 |
| 8,569,210 B2 | 10/2013 | Fefer et al. |
| 8,747,874 B2 | 6/2014 | Fefer |
| 8,853,128 B2 | 10/2014 | Fefer et al. |
| 9,226,504 B2 | 1/2016 | Fefer et al. |
| 9,259,004 B2 | 2/2016 | Norton et al. |
| 9,357,768 B2 | 6/2016 | Fefer et al. |
| 9,451,773 B2 | 9/2016 | Fefer et al. |
| 9,485,988 B2 | 11/2016 | Fefer et al. |
| 2003/0194454 A1 | 10/2003 | Bessette et al. |
| 2004/0192551 A1 | 9/2004 | Bessette |
| 2005/0181949 A1 | 8/2005 | Norton et al. |
| 2005/0274164 A1 | 12/2005 | Coates et al. |
| 2006/0068991 A1 | 3/2006 | Norton et al. |
| 2008/0085832 A1 | 4/2008 | Fefer et al. |
| 2009/0325922 A1 | 12/2009 | Fefer et al. |
| 2010/0016447 A1 | 1/2010 | Fefer |
| 2011/0197320 A1 | 8/2011 | Kweon |
| 2012/0186150 A1 * | 7/2012 | Yadav .................. A01G 31/001 47/48.5 |
| 2015/0018211 A1 | 1/2015 | Rees et al. |

FOREIGN PATENT DOCUMENTS

| | | | |
|---|---|---|---|
| CN | 101289342 | * | 10/2008 |
| CN | 104446962 | * | 3/2015 |
| DE | 2511077 A1 | | 9/1976 |
| EP | 1563734 A1 | | 8/2005 |
| JP | S4993413 A | | 9/1974 |
| JP | S5196446 A | | 8/1976 |
| JP | S644677 A | | 1/1989 |
| JP | H01157904 A | | 6/1989 |
| JP | H01219723 A | | 9/1989 |
| JP | H02250801 A | | 10/1990 |
| JP | H03221576 A | | 9/1991 |
| JP | H04314769 A | | 11/1992 |
| JP | H069323 A | | 1/1994 |
| JP | H06279162 A | | 10/1994 |
| JP | H09272818 A | | 10/1997 |
| JP | H10234231 A | | 9/1998 |
| JP | H11137084 A | | 5/1999 |
| JP | H11228859 A | | 8/1999 |
| JP | H11346576 A | | 12/1999 |
| JP | 2002293706 A | | 10/2002 |
| WO | WO-1993012175 A1 | | 6/1993 |
| WO | WO-1996032010 A2 | | 10/1996 |
| WO | WO-1996032011 A2 | | 10/1996 |
| WO | WO-2009049747 A2 * | 4/2009 | ............ A01N 43/16 |
| WO | WO-2012171126 A1 * | 12/2012 | ............ A01N 27/00 |
| WO | WO-2015081441 A1 * | 6/2015 | ............ A01N 43/90 |

OTHER PUBLICATIONS

By Llic et al.(Effect of coloured shade-nets on plant leaf parameters and tomato fruit quality, J. Sci. Food Agric. 2015, 95: 2660-7). (Year: 2015).*

(Continued)

*Primary Examiner* — Alton N Pryor

(74) *Attorney, Agent, or Firm* — Foley Hoag LLP

(57) ABSTRACT

A method for enhancing or reducing photosynthetic activity, wherein non-toxic pigmented matter is applied to a photosynthetic organism. Depending on the composition of the pigmented matter, the method will have the effect of enhancing, reducing, or inhibiting photosynthetic activity.

6 Claims, 6 Drawing Sheets

(56) References Cited

OTHER PUBLICATIONS

Beck, "Why the Peacock Begonia Has Beautiful Blue Leaves," The Christian Science Monitor (Oct. 25, 2016).
Cleary Chemical Corporation, "Use of Cleary's Grass Greenzit", p. 1, Technical Information (2004).
Diesburg "Effects of Turf Colorants and FeS04 on Spring Greenup of Zoysia Grass," pp. 1-2 (1990), http://www.turf.uiuc.edu/research/summaries/1990/effect-colorant.pdf.
Jacobs et al., "Photonic Multilayer Structure of Begonia Chloroplasts Enhances Photosynthetic Efficiency," Nat Plants, 2(11): 16162 (2016).
Kopeck et al., "Overseed Greens Performance Trials," (1995-1996).
Liu et al., "Cytokinin effects on creeping bentgrass responses to heat stress: I. Shoot and root growth," Crop Sci, 42(2): 547-465 (2002).
Morris, A Guide to NTEP Turfgrass Ratings, http://www.ntep.org/reports/ratings.htm, pp. 1-4, (2011).
Service, "Blue Leaves Help Plants Get Extra Energy from Sun," Science (2016).
Vaiciunas et al., "Bentgrass dead spot: a new disease of golf course greens and trees," Rutgers University, 77-79.
Van Dam et al., "A Turfgrass Colorant Study," California Turfgrass Culture, 21(3): 17-24 (1971).
Younger, "Kikuyugrass, Pennisetum clandestinum, and its Control," Southern Cailfornia Turfgrass Culture, 8(1): 1-8 (1958).
"Colored Shade Nets for Improved Apple Quality and Yield," published in Israel Agriculture, pp. 1-3 (Aug. 31, 2014).
Ilić et al., "Effect of coloured shade☐nets on plant leaf parameters and tomato fruit quality," J Sci Food Agric, 95:2660-2667 (2015).
Shahak et al., "ColorNets: Crop protection and light-quality manipulation in one technology," Acta Hort, 659:143-151 (2004).
Shahak et al., "Improving solar energy utilization, productivity and fruit quality in orchards and vineyards by photoselective netting," Acta Hortic, 772:65-72 (2008).
Stamps, "Use of colored shade netting in horticulture," HortScience, 44(2)239-241 (2009).

\* cited by examiner

FIG. 1

| Color | Effect |
|---|---|
| Green | Growth |
| Blue | Growth |
| Yellow | Stops growth and causes wilting and subsequent cell death |
| Red | Stops growth and kills plant |
| Black | Stops growth and kills plant by blocking light absorption |

FIG. 2

| Food Coloring | Ingredients |
|---|---|
| Green | Water. Propylene Glycol, FD&C Yellow 5, FD&C Blue 1 and Propylparaben |
| Blue | Water. Propylene Glycol, FD&C Blue 1 and Red 40, and Propylparaben |
| Yellow | Water. Propylene Glycol, FD&C Yellow 5, Propylparaben, and Red 40 |
| Red | Water. Propylene Glycol, FD&C Reds 40 AND 3, and Propylparaben |
| Black | Water, FD&C Red 40, FD&C Blue 1, FD&C Yellow 5, Phosphoric Acid, and Sodium Benzoate |

FIG. 3

| Days | Red Pigment | Yellow Pigment | Green Pigment | Blue Pigment |
|---|---|---|---|---|
| 1 | Pigment can be seen rising in stem. | Pigment can be seen rising in stem. | Pigment can be seen rising in stem. | Pigment can be seen rising in stem. |
| 2 | Pigment can be seen rising in stem and leaves. | Pigment can be seen in stem and leaves. | Pigment can be seen in stem and leaves. | Pigment can be seen in stem and leaves. |
| 3 | Pigment can be seen in stem and leaves. Leaves are less green, more red and less taut. | Pigment can be seen in stem and leaves. Leaves are less green, more yellow and less taut, but more taut than the plant in red pigment. | Pigment can be seen in stem and leaves. Leaves are greener and more taut. | Pigment can be seen in stem and leaves. Leaves are blue/green and more taut. |
| 4 | Pigment can be seen in stem and leaves. Leaves are less green, more red and less taut. | Pigment can be seen in stem and leaves. Leaves are less green, more yellow and less taut, but more taut than the plant in red pigment. | Pigment can be seen in stem and leaves. Leaves are greener and more taut. | Pigment can be seen in stem and leaves. Leaves are darker blue/green and more taut. |
| 5 | Pigment can be seen in stem and leaves. Leaves are red/yellow and wilting. | Pigment can be seen in stem and leaves. Leaves are yellow and wilting. | Pigment can be seen in stem and leaves. Leaves are generally a deep green, taut, and the plant looks robust. The leaves are thicker and firmer on palpation. | Pigment can be seen in stem and leaves. Leaves are generally a deep green/blue, taut, and the plant looks robust. The leaves are thicker and firmer on palpation than all other pigments. |

FIG. 3 (cont.)

| 6 | Pigment can be seen in stem and leaves. Leaves are red/yellow and wilting.<br><br>Edges of leaves are turning brown and dried up. | Pigment can be seen in stem and leaves. Leaves and stem are yellow and there is significant wilting of stem and leaves. | Pigment can be seen in stem and leaves. Leaves are generally a deep green, taut, and the plant looks robust. The leaves are thicker and firmer on palpation. | Pigment can be seen in stem and leaves. Leaves are generally a deep green/blue, taut, and the plant looks robust. The leaves are thicker and firmer on palpation than all other pigments. |
|---|---|---|---|---|
| 7 | Pigment can be seen in stem and leaves. Leaves are red/yellow and wilting. Edges of leaves continue to turn brown and dry up. | Pigment can be seen in stem and leaves. Leaves and stem are yellow and there is significant wilting of stem and leaves. | Pigment can be seen in stem and leaves. Leaves are generally a deep green, taut, and the plant looks robust. The leaves are thicker and firmer on palpation. | Pigment can be seen in stem and leaves. Leaves are generally a deep green/blue, taut, and the plant looks robust. The leaves are thicker and firmer on palpation than all other pigments. |

FIG. 4

| Days | Red Pigment | Orange Pigment | Yellow Pigment | Green Pigment | Blue Pigment | Purple Pigment |
|---|---|---|---|---|---|---|
| 1 | Pigment can be seen rising in stem. | Pigment can be seen rising in stem. | Pigment can be seen rising in stem. | Pigment can be seen rising in stem. | Pigment can be seen rising in stem. | Pigment can be seen rising in stem. |
| 2 | Pigment can be seen rising in stem and leaves. | Pigment can be seen rising in stem and leaves. | Pigment can be seen in stem and leaves. | Pigment can be seen in stem and leaves. | Pigment can be seen in stem and leaves. | Pigment can be seen rising in stem and leaves. |
| 3 | Pigment can be seen in stem and leaves. Leaves are less green, more red and less taut. | Pigment can be seen in stem and leaves. Leaves are less green, more orange and less taut. | Pigment can be seen in stem and leaves. Leaves are less green, more yellow and less taut, but more taut than the plant in red pigment. | Pigment can be seen in stem and leaves. Leaves are greener. | Pigment can be seen in stem and leaves. Leaves are blue/green. The leaves are less taut than the green pigment. | Pigment can be seen in stem and leaves. Leaves contain purple and are less taut than the green or blue pigment. |

FIG. 4 (cont.)

| 4 | Pigment can be seen in stem and leaves. Leaves are less green, more red, and wilting. | Pigment can be seen in stem and leaves. Leaves and stem are less green, more orange and wilting. | Pigment can be seen in stem and leaves. Leaves are less green, more yellow and wilting but has less significant wilting compared with red and orange pigment. | Pigment can be seen in stem and leaves. Leaves are greener but not thriving. | Pigment can be seen in stem and leaves. Leaves are darker blue/green but loosing tautness. | Pigment can be seen in stem and leaves. Leaves and stem contain purple and are wilting. |
| --- | --- | --- | --- | --- | --- | --- |
| 5 | Pigment can be seen in stem and leaves. Leaves are red/yellow and wilting. | Pigment can be seen in stem and leaves. Leaves and stem are less green, more orange and wilting. | Pigment can be seen in stem and leaves. Leaves are yellow and wilting. | Pigment can be seen in stem and leaves. Leaves are a deeper green but losing tautness. | Pigment can be seen in stem and leaves. Leaves are a deep green/blue. The stem and leaves are wilting significantly. | Pigment can be seen in stem and leaves. Leaves and stem contain purple and are wilting more significantly compared to blue. |

FIG. 5

| Pigment | 7 days | 14 days |
|---|---|---|
| Green | Grass remained green and appeared slightly heartier | Grass remain green and appeared slightly heartier |
| Blue | Grass remained blue | Grass remained blue |

FIG. 6

| Weed (Red pigment) | Leafy Plant (Green pigment) |
|---|---|
| Leaves showed significant wilting after 7 days | Plant thriving after 7 days |
| Weed nearly completely dead after 14 days | Plant thriving after 14 days |

METHOD FOR ALTERING PHOTOSYNTHETIC GROWTH

PRIORITY

This application claims the benefit of provisional patent application Ser. No. 62/104,797 filed in the United States Patent and Trademark Office on Jan. 18, 2015, the entire contents of which are incorporated by reference herein.

INTRODUCTION

The use of conventional fertilizers and pesticides contaminate our drinking water supply and adversely affect ecosystems and wildlife in the areas where they are applied and, more extensively, through runoff. Certain cancers and reproductive problems, among other medical conditions, have been related to the use of fertilizers and pesticides, both through direct exposure and through runoff. As a result, the World Health Organization (WHO) announced findings that glyphosate, the most popular weed killer globally, is a probable carcinogen; the number of lawsuits is increasing; California has moved to label glyphosate as carcinogenic; and states for several years have been incentivizing greener lawn care to reduce pollution from runoff. Thus, there is a need for a process to enhance or inhibit plant growth, similar to conventional fertilizers and pesticides, but without the adverse effects.

Presently, there are no fertilizers or pesticides that implement non-toxic, pigmented matter to alter photosynthetic activity without adversely affecting the environment or human health. While there are all-natural fertilizers and pesticides available on the market, none of them are both all-natural and make use of the sun's renewable energy. Further, some all-natural fertilizers have been linked to infectious disease outbreaks.

Photosynthetic organisms use pigments to absorb light energy, which they subsequently convert into chemical energy for food via photosynthesis. Plants and certain other photosynthetic organisms contain several types of pigments. Each pigment absorbs light concentrated at specific wavelengths. The absorption of energy from light promotes vegetative growth and enhances nutrients. In many photosynthetic organisms, red light is absorbed to a lesser degree than blue light, although absorption rates may vary depending on the type of plant and the time of year. Red light promotes flowering and budding of plants and provides energy that is converted into food, among other things. Blue light enables chloroplast movement, phototropism, stomatal opening, and seedling growth regulation, among other things.

Chlorophyll is a primary pigment found in most photosynthetic organisms. Chlorophyll-a, $C_{55}H_{72}O_5N_4Mg$, is a dominant pigment occurring in all photosynthetic organisms, including cyanobacteria. Chlorophyll-a exhibits a green color and absorbs mostly blue and red light, with absorption peaks at approximately 430 nm and 662 nm, respectively. Absorption peaks represent the wavelengths of light energy that are absorbed at the greatest magnitude by the absorbing medium. Thus, out of all of the colors on the electromagnetic spectrum, chlorophyll-a absorbs blue (430 nm) and red (662 nm) light at the greatest magnitude. Chlorophyll-b, $C_{55}H_{70}O_6N_4Mg$, is a pigment found in all plants, green algae and some prokaryotes. Chlorophyll-b is blue-green in color with absorption peaks at approximately 453 nm and 642 nm, which, similarly to chlorophyll-a, represent blue and red light waves, respectively Carotenoids are another family of pigments found in all photosynthetic organisms, and appear red, yellow or orange in color. Carotenoids are accessory pigments in plants and work as adjuvant absorbers of light, by extending the range of wavelengths over which light can drive photosynthesis. The energy carotenoids absorb from light is transferred to the chlorophyll, which then uses the light energy in photosynthesis. In the fall, when chlorophyll is no longer present in leaves, carotenoids exist for a time. The presence of carotenoids without chlorophyll makes leaves appear yellow. Eventually, leaves that lack chlorophyll for an extended period of time will die. One of the most important carotenoids used in photosynthetic organisms is Beta-carotene, $C_{40}H_{56}$.

The third major pigment in some plants are anthocyanins, which exhibit a red color and are seen in the fall. Anthocyanins form when concentrated sugars react with light and certain proteins in cell sap.

On their own, land plants convert only about 2% to 4% of the available sunlight into glucose through the process of photosynthesis. As the density of certain pigments in plants increases, wavelengths of light are absorbed more efficiently and at a greater magnitude. Adding green pigment to green leaves increases the density of the green pigment in the leaves, which in turn increases light absorption. For example, plants that commonly grow in the shade have increased relative concentrations of green pigments, so they can more efficiently harvest sunlight at low light levels. In contrast, adding red or certain other pigments to green plants prevents the plant from absorbing solar energy at the wavelengths it needs for photosynthesis, thus reducing or inhibiting photosynthetic activity. Yellow pigments work in a similar fashion to red pigments, but because they are closer to green on the electromagnetic spectrum, yellow pigments do not block as much solar energy. Thus, when yellow pigments are applied to plants, the plants die more slowly than they would with the application of red pigments. Plants and other organisms that are not green will respond in a similar fashion with different pigments. Similarly, black pigment will absorb light and white pigment will reflect light in photosynthetic organisms.

The present method relates to more efficient and potentially less expensive means to alter growth in photosynthetic organisms, such as plants, algae, and certain bacteria, by applying non-toxic, pigmented matter to the photosynthetic organism. Examples of such pigmented matter may include, but are not limited to, synthetic pigments and compounds that have been derived from plants, invertebrates, or minerals, including: vegetable dyes, food coloring, and plant pigments such as chlorophyll, carotenoids, or flavonoids.

It is an object of the present method to provide a solution to the human health and environmental problems associated with conventional fertilizers and pesticides used on lawns and on farms, as well as other places. It is another object of the present method to provide a simple, inexpensive solution to enhance crop growth internationally by providing a second use of existing product, such as food colorings, where the food colorings may be, but are not limited to, liquid, powder, gel, or pellet form. It is another object of the present method to enhance or increase the nutrients a plant produces by adding non-toxic and environment-friendly pigmented matter, such as food colorings, for example. It is yet another object of the present method to change or deepen the colors of flowers, fruits and vegetables by facilitating targeted photosynthesis with non-toxic and environment-friendly pigmented matter, such as food colorings for example, where the enzyme would be used as part of the product. It is yet another object of the present method to inhibit unwanted plant growth with non-toxic and environment-friendly pigmented matter, such as food colorings, for example.

BRIEF DESCRIPTION OF THE DRAWINGS

FIG. 1 shows the specific effects that different pigments have on photosynthetic activity after being provided to green plants.

FIG. 2 shows the chemical compounds of certain food colorings, which can be provided to photosynthetic organisms to alter photosynthetic activity.

FIG. 3 shows the visible results observed when various pigments were applied to green plants in a natural light setting.

FIG. 4 shows the visible results observed when various pigments were applied to green plants in a fluorescent light setting.

FIG. 5 shows the visible results observed when blue and green pigments were applied to grass.

FIG. 6 shows the visible results observed when red pigments were applied to weeds and green pigments were applied to leafy plants.

DETAILED DESCRIPTION OF CERTAIN EMBODIMENTS OF THE INVENTION

The present method involves the application of pigmented matter, alone or in combination with other agents or substances, to photosynthetic organisms. This application can work to enhance or reduce absorption of certain wavelengths of light, which, in turn, enhances or reduces photosynthetic activity. Photosynthetic activity is a measurement of the light absorption efficiency of the plant, which in turn affects the amount of energy produced by photosynthesis. For example, as shown in FIG. 1, providing blue and green pigments to green plants enhances photosynthetic activity in the plant by enabling the plant to absorb light energy at a greater magnitude, which in turn increases the output of chemical energy produced by the plant. The increase of photosynthetic activity in a plant will cause a number of changes in the plant's physical appearance, including but not limited to, a faster growth rate, more robust leaves and stems, heartier leaves and stems, and firmer leaves and stems, and may deepen the color of the leaves and stems of a plant and enhance or increase its nutrients. Thus, the method of providing blue and green pigments to green plants may be used in place of or in addition to a reduced amount of conventional fertilizers. For example, as shown in FIG. 3, one plant with multiple branches was separated and each branch was placed in one of four cups of water. Each of the four cups contained 6 drops of either red, yellow, green, or blue pigment (one pigment per cup) mixed into the water. The cups were then placed on a table about 6 feet from a sliding glass door opening to natural sunlight, which served as its main light source. The cups were lined up next to each other, perpendicular to the light source with red placed closest to the window, then yellow, green, and the blue cup being the farthest from the window. Over a period of 7 days, the branches that were placed in the cups with blue and green pigment were observed to be more robust, with a deeper green, and more taught, thicker, and firmer leaves on palpation.

Similarly, as shown in FIG. 5, a gallon of highly diluted green pigment in water was applied to a 6-inch by 6-inch area of grass during the winter months in the Mid Atlantic region, and observed after 7 days, and again after 14 days. At the end of the 7 and 14-day periods, the grass was observed to have remained green and appeared slightly heartier than before the application of the green pigment. Further, as shown in FIG. 6, when a 100% concentration of green pigment was applied directly to the leaves of a leafy plant during the summer months, the plant was observed to be thriving after 14 days.

Other pigments may be added to green plants to reduce photosynthetic activity, as shown in FIG. 1. For example, adding red pigment to a green plant effectively blocks light absorption by the plant, which in turn reduces or inhibits photosynthetic activity, causing the plant to eventually die. Similarly, yellow and any other pigment that blocks the absorption of light, reduces or prevents photosynthetic activity in green plants. Thus, a variation of red, yellow and and/or other light-blocking pigments, may be applied to green plants in place of conventional herbicides and pesticides. Thus, as shown in FIG. 3, branches that were placed in cups of yellow and red pigment were observed to develop wilting stems and leaves over a period of seven days. Further, as shown in FIG. 6, 100% red pigment was applied directly to the leaves of an aggressive weed with an expanse of >12 inches during the summer months in the Mid Atlantic region. After a period of 7 days, the weed leaves showed significant wilting, and after the 14-day mark, the weed was almost completely dead.

FIG. 4 shows the results observed when multiple branches of a plant were separated and placed into 6 cups of water, each with 6 drops of either red, yellow, orange, green, blue or purple pigment mixed into 12 ounces of water. The cups were placed on a counter top under artificial fluorescent light with a dark curtain covering any access to natural sunlight. Over a period of 5 days, all 6 branches appeared to be wilting to one degree or another. These results are consistent with the use of fluorescent light instead of natural sunlight. This is because fluorescent light lacks many of the red and blue light wavelengths that are found in natural sunlight. As a result, the plants receiving the blue and green pigments that would normally thrive under natural sunlight, could not thrive because there were not enough blue and red light wavelengths available to be absorbed for photosynthetic enhancement.

The process of inhibiting or enhancing plant growth has been used for centuries as a way to increase or decrease crop and plant yield in the agricultural and horticultural sectors. Currently, pesticides and herbicides are used to inhibit growth and kill plants and weeds that would otherwise decimate target plants and crops through competition for space and nutrients. By killing these competitive plants and weeds, the target plants and crops are able to thrive. A method of using non-toxic, pigmented matter to inhibit plant growth in a similar fashion may be used in place of those conventional pesticides and herbicides to produce a similar growth-inhibiting effect. Likewise, fertilizers are used to enhance growth in target plants and crops, a desired outcome in the agricultural and horticultural sectors. Conventional fertilizers work by improving the fertility of the soil in which a plant grows, thus allowing the plant to absorb more nutrients than it would under normal circumstances. The end result is a healthier, and potentially larger plant. A method of using non-toxic, pigmented matter to enhance plant growth may be used in place of or in addition to conventional fertilizers to produce similar growth-enhancing effects.

One embodiment of the method involves application of growth-enhancing pigmented matter, such as various shades of blue and green matter, which, whether alone or in combination with other agents or substances, can enhance photosynthetic activity. Another embodiment of the method involves application of growth-inhibiting pigmented matter, such as various shades of red, and yellow, either alone or in combination with other agents or substances, which reduce or inhibit photosynthetic activity. These embodiments of the present method do not exclude adjuvants, such as enzymes.

One example of such a pigmented matter is food coloring, where food coloring may include but is not limited to FD&C Blue No. 1 ($C_{37}H_{34}N_2Na_2O_9S_3$), FD&C Red No. 3 ($C_{20}H_6I_4Na_2O_5$), FD&C Red No. 40 ($C_{18}H_{14}N_2Na_2O_8S_2$), and/or FD&C Yellow No. 5 ($C_{16}H_9N_4Na_3O_9S_2$).

The present method further contemplates that food color dyes may be appropriately mixed. For example, FD&C Yellow No. 5 can be mixed with FD&C Red. No. 40 in a 3:1 ratio, respectively, to create an orange color. Moreover, food color dye and dye mixtures can be concentrated or diluted, depending on the plant, soil, weather conditions, and/or desired outcome, among other factors. In one non-limiting example, a single dye, such as FD&C Blue No.1, may be diluted by at least 1% with water (for example, a single dye may be diluted by 1%, 10%, 20%, 35%, 40%, 50%, 60%, 75%, 80%, 90%, or 99% with water).

Application of such pigmented matter can be achieved through various methods. In one preferred embodiment, the method would involve spraying the leaves and/or stem of the plant with the pigmented matter. This method may be carried out through the use of a pigmented solution or liquid suspension, which is then sprayed (using, for example, a dusting or misting apparatus and/or a spray bottle) directly onto the leaves and/or stem of the photosynthetic organism.

Another such method may involve wiping the leaves and/or stem of the plant with the pigmented matter. This method may be carried out through the use of a pigmented solution, gel, dust, or powder, and may be applied by hand, or via a mechanical device.

Another such method may involve spraying the soil with the pigmented matter. This method may be carried out through the use of a pigmented solution or liquid suspension, which is then sprayed (using, for example, a dusting or misting apparatus and/or a spray bottle) directly onto the soil in which the photosynthetic organism grows.

Another method may involve irrigating the soil with a pigmented solution. This method may be carried out by first dissolving the pigmented matter into water, and then applying the resulting pigmented solution to the soil through various irrigation devices. One such irrigation device may be sprinkler system. Another such irrigation device may include pipes or porous tubing placed below the ground, which operate under lower pressure and release the pigmented solution into the soil at a desired rate.

Another method may involve soaking the seeds of plants in a pigmented solution. This method may be carried out by first preparing a solution of pigmented matter, which may include a food coloring diluted with water to a desired concentration. Next, a bowl, basin, or other container is filled with the pigmented solution, and the plant seeds are placed in the solution for a desired period of time before planting. The period of soaking time depends on the type of seed being used, and can range anywhere from around 20 minutes to 24 hours or more. For example, larger seeds with harder shells may be soaked for longer periods of time, while smaller seeds with softer shells may be soaked for shorter periods.

Another method may involve injecting the pigmented matter as a liquid suspension or solution into the soil or other media in which the plant or other organism is growing. This method may be carried out using a probe or injection pipe. The probe or injection pipe may be inserted directly into the target soil or other media through mechanical means, such as through the use of a drill. The probe or injection pipe may then inject the pigmented solution, which is fed from a supply tank, into the surrounding soil or other media. The composition of the pigmented solution used may, for example, be blue food dye mixed with water in a 3:1 ratio, respectively.

Another method may involve mixing pigmented matter with other agents, such as fertilizers, vitamins, or other plant nutrients. This method may be carried out by soaking the fertilizer, vitamins or other plant nutrients in a pigmented solution for desired period of time. For example, 6-12 hour soak may be appropriate for more porous fertilizers, vitamins or nutrients, while a longer, 24-hour soak may be appropriate for less porous fertilizers, vitamins or nutrients. After the soaking period is complete, the fertilizer, vitamin, or nutrient may be sprayed onto the soil or other media, leaves and/or stem, inserted directly into the soil or other media, or be dissolved in water, which is then applied to the soil or other media in which the plant is growing.

Another method may involve adding a pigmented liquid, such as blue or green food coloring, or a pigmented solution, to shredded or cut up material, for example, shredded newspaper, straw or plastic. In one embodiment of this method, food coloring is applied to shredded newspaper, and the resulting colored newspaper is used to cover newly planted seeds to protect them from certain growth-disruptive environmental conditions, such as wind, heavy rain, or animal activity. Further, both the nutrients in the paper and the food coloring will seep into the ground, seeds, and roots after water is applied via rainfall or mechanical watering methods.

Another method may involve mixing pigmented matter with an adhesive, such as glue. The pigmented matter may be mixed with a base liquid adhesive to create a solution or liquid suspension, which may then be applied to the plant or organism by spraying the solution directly onto the soil in which the plant grows, or directly onto plant leaves and/or stem.

Another method may involve applying an adhesive or adhesive-solution by itself to the plant directly or onto the soil in which the plant grows. This method may be carried out for example, by spraying the adhesive onto the soil, or leaves and/or stem of a plant and subsequently spraying on a pigmented solution. This method will ensure that any pigmented matter provided will properly adhere to the plant or soil.

Another method may involve diluting pigmented matter in alcohol, with or without other agents or substances. The pigmented alcohol solution may then be sprayed (using, for example, a dusting or misting apparatus and/or a spray bottle) directly onto the soil, or onto the leaves and/or stem of the plant.

Another method may involve adding pigment to a solution used to feed plants in a hydroponic setting.

Finally, the present method may be applied to other organisms that rely on photosynthesis for growth, such as algae and certain bacteria that grow in water. Application of the pigmented matter to such organisms may be achieved by various methods.

One such method may involve preparing a pigmented solution or liquid suspension, which is then sprayed onto photosynthetic bacteria or algae growing in water. The pigmented solution may be mixed with a surfactant, to ensure proper diffusion of the solution in water. The solution may then be sprayed (using, for example, a misting apparatus and/or a spray bottle), directly onto the algae or bacteria that grow on or near the surface of the water.

Another such method may involve injecting a pigmented solution or liquid suspension into water in which photosynthetic bacteria or algae is growing. The pigmented solution may be mixed with a surfactant, to ensure proper diffusion of the solution in water. The solution may then be injected directly into the water in which the algae or bacteria grow.

Another method may involve immersing photosynthetic bacteria or algae in a pigmented solution or targeting in a lake or other body of water. This method may be carried out by first preparing a solution of pigmented matter, which may include a food coloring diluted with water to a desired concentration. Next, a bowl, basin or other container is filled with the pigmented solution, and the target algae or bacteria are immersed in the solution for a period of 12-48 hours, or longer.

What is claimed is:

1. A method for reducing or enhancing photosynthetic activity of a photosynthetic organism, the method consisting essentially of providing a form of pigmented matter, fertilizer, and optionally an adhesive material to the photosynthetic organism, wherein the pigmented matter is sprayed onto the leaves of the photosynthetic organism, and the pigmented matter contains chlorophyll.

2. The method of claim 1, further comprising: applying the adhesive material to the leaves of the photosynthetic organism before the pigmented matter is sprayed onto the leaves.

3. The method of claim 1, wherein the photosynthetic activity of a weed is reduced.

4. The method of claim 1, wherein the photosynthetic activity of a plant is enhanced.

5. The method of claim 1, wherein the photosynthetic organism is a plant.

6. The method of claim 2, wherein the photosynthetic organism is a plant.

* * * * *